Aug. 5, 1975 F. W. ANDERSON Plant Pat. 3,759
NECTARINE TREE
Filed Sept. 23, 1974
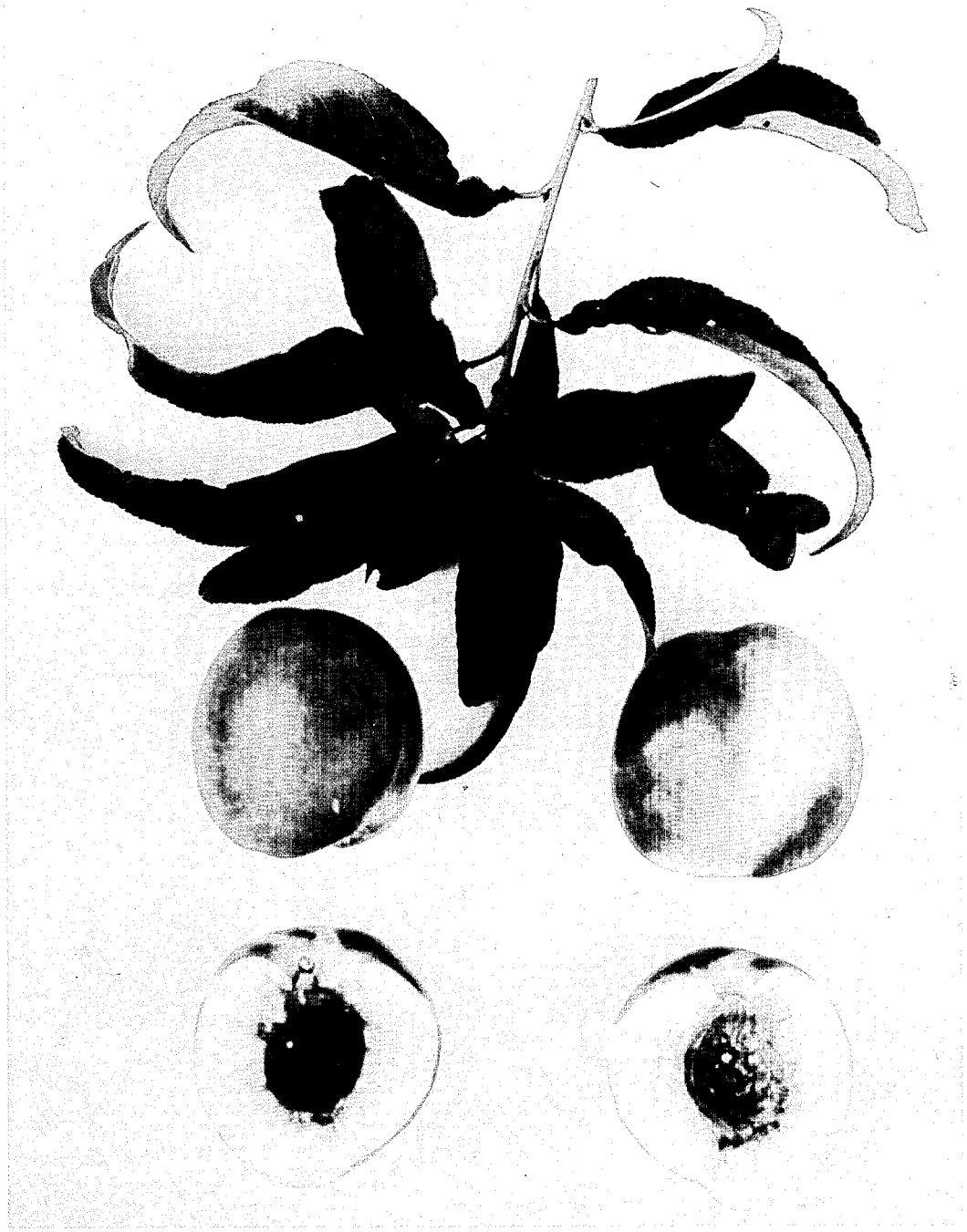

United States Patent

Plant Pat. 3,759
Patented Aug. 5, 1975

3,759
NECTARINE TREE

Frederic W. Anderson, Merced, Calif., assignor to
The Burchell Nursery, Inc., Modesto, Calif.

Filed Sept. 23, 1974, Ser. No. 508,701
Int. Cl. A01h *5/03*
U.S. Cl. Plt.—41 1 Claim

ABSTRACT OF THE DISCLOSURE

A nectarine tree which is vigorous, upright to spreading, open, foliated with medium size, lanceolate leaves with a crenate margin, and a very productive bearer of uniform, symmetrical, globose, medium size, freestone fruit having yellow skin substantially overspread with red partially mottled and streaked, yellow flesh, and a red pit cavity with the red streaked into the flesh.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery located as aforesaid, as a cross between the Red Free nectarine (U.S. Plant Pat. No. 3,328) as the seed parent, and the Autumn Gold nectarine (U.S. Plant Pat. No. 3,478) as the pollen parent. Seedlings resulting from such cross were grown by me under conditions of careful and continuing observation, and one—which is the present variety—evidenced substantial novelty and was, therefore, selected for asexual reproduction and in contemplation of ultimate commercialization.

ASEXUAL REPRODUCTION OF THE VARIETY

The present variety of nectarine tree was successfully asexually reproduced by me, in my said orchard, by topworking on existing young trees therein, and—in maturity—such reproductions ran true to the original tree in all respects.

SUMMARY OF THE VARIETY

The present variety of nectarine tree is vigorous, upright to spreading, open, foliated with medium size, lanceolate leaves with a crenate margin, and a very productive bearer of uniform, symmetrical, globose, medium size, freestone fruit having yellow skin substantially overspread with red partially mottled and streaked, yellow flesh, and a red pit cavity with the red streaked into the flesh; the variety, which in general resembles the Red Free nectarine, the seed parent, is characterized, in comparison, by ripening about three weeks later, thus desirably extending the harvest season for such type of freestone nectarine.

BRIEF DESCRIPTION OF THE DRAWING

The drawing is an illustration, by photographic reproduction in color, of a twig with leaves, and separate fruit; one of the latter being cut into halves to expose the flesh, and with the stone remaining in one half.

DESCRIPTION OF THE VARIETY

The botanical details of this new and distinct variety of nectarine tree—with color definitions referenced to Maerz and Paul Dictionary of Color—are as follows:

TREE
- *Vigor.*—Vigorous.
- *Growth.*—Upright to spreading.
- *Density.*—Open.
- *Production.*—Very productive.

TRUNK
- *Size.*—Medium.

BRANCHES
- *Size.*—Medium.

LEAVES
- *Size.*—Medium. Average length—6½". Average width—¾".
- *Form.*—Lanceolate.
- *Thickness.*—Medium.
- *Margin.*—Crenate.
- *Petiole.*—Medium length. Medium thickness.
- *Glands.*—Average number and position—usually 2 on petiole and 2 on blade. Alternate. Medium size. Reniform.
- *Color.*—Top side—Medium green (23–L–7). Under side—Lighter green (22–K–5).

FLOWER BUDS
- *Size.*—Medium.

FLOWERS
- *Blooming period.*—About with Sun Grand nectarine (U.S. Plant Pat. No. 974). Medium, as compared with other varieties.
- *Size.*—Large.

FRUIT
- *Maturity when described.*—Eating ripe—Aug. 29, 1974.
- *Date of first picking.*—Aug. 15, 1974.
- *Date of last picking.*—Aug. 25, 1974.
- *Size.*—Uniform. Medium. Average diameter axially—2⅜". Average transversely in suture plane—2 5/16".
- *Form.*—Uniform. Symmetrical. Globose.
- *Suture.*—Distinct. Shallow. Extends from base to beyond apex, with marked depression beyond pistil point.
- *Ventral surface.*—Rounded.
- *Cavity.*—Elongated in suture plane, with suture showing on one side.
- *Apex.*—Depressed.
- *Pistil point.*—Very short. Inconspicuous.

SKIN
- *Thickness.*—Medium.
- *Texture.*—Medium.
- *Tendency to crack.*—None.
- *Color.*—Yellow (10–L–3) substantially overspread with red (5–L–6) (partially mottled and streaked) shading to darker red (7–L–6).

FLESH
- *Juice.*—Moderate.
- *Texture.*—Firm. Crisp. Meaty.
- *Ripens.*—Evenly.
- *Flavor.*—Sub-acid. Vinous.
- *Eating quality.*—Good to best.
- *Color.*—Yellow (10–L–5).
- *Surface of pit cavity.*—Red (5–L–6) with red streaked into the flesh.

STONE
- *Type.*—Free.
- *Size.*—Medium. Average length—1⅛". Average breadth—⅞". Average thickness—¾".
- *Form.*—Oblong. Obovoid.
- *Base.*—Straight.
- *Apex.*—Rounded.
- *Sides.*—Equal.

*Tendency to split.*—Very slight.

*Color.*—Brown (56–H–3).

USE

Market. Local and long distance shipping.

KEEPING QUALITY

Good.

RESISTANCE TO INSECTS AND DISEASES

No unusual susceptibilities noted.

SHIPPING QUALITY

Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is vigorous, upright to spreading, open, foliated with medium size, lanceolate leaves with a crenate margin, and a very productive bearer of uniform, symmetrical, globose medium size, freestone fruit having yellow skin substantially overspread with red partially mottled and streaked, yellow flesh, and a red pit cavity with the red streaked into the flesh; the variety, which in general resembles the Red Free nectarine, the seed parent, is characterized, in comparison, by ripening about three weeks later, thus desirably extending the harvest season for such type of freestone nectarine.

No references cited.

ROBERT E. BAGWILL, Primary Examiner